US007407118B2

(12) United States Patent
Sevy

(10) Patent No.: US 7,407,118 B2
(45) Date of Patent: Aug. 5, 2008

(54) ATOMIZATION JET ASSEMBLY

(76) Inventor: Earl Vaughn Sevy, 4560 N. Tomahawk Dr., Enoch, UT (US) 84720

( * ) Notice: Subject to any disclaimer, the term of this patent is extended or adjusted under 35 U.S.C. 154(b) by 503 days.

(21) Appl. No.: 10/821,677

(22) Filed: Apr. 8, 2004

(65) Prior Publication Data

US 2005/0077383 A1 Apr. 14, 2005

Related U.S. Application Data

(60) Provisional application No. 60/464,664, filed on Apr. 10, 2003.

(51) Int. Cl.
*B05B 7/30* (2006.01)
*A61M 11/00* (2006.01)

(52) U.S. Cl. ....................... 239/347; 239/338; 239/342; 128/200.18; 128/200.21

(58) Field of Classification Search ................. 239/338, 239/340, 343, 346, 347, 366–370, 424, 386, 239/387; 128/200.21, 200.18, 200.14, 194
See application file for complete search history.

(56) References Cited

U.S. PATENT DOCUMENTS

| | | | | |
|---|---|---|---|---|
| 2,826,454 | A | 3/1958 | Coanda | |
| 2,869,188 | A | 1/1959 | Camento | |
| 3,077,307 | A | 2/1963 | Moore | |
| 3,584,792 | A | 6/1971 | Johnson | |
| 3,762,409 | A | 10/1973 | Lester | |
| 4,007,238 | A * | 2/1977 | Glenn | 261/78.2 |
| 4,333,450 | A | 6/1982 | Lester | |
| 4,512,341 | A * | 4/1985 | Lester | 128/200.21 |
| 4,566,452 | A | 1/1986 | Farr | |
| 4,588,129 | A | 5/1986 | Shanks | |
| 4,657,007 | A | 4/1987 | Carlin et al. | |
| RE33,717 | E | 10/1991 | Svoboda | |
| 5,072,883 | A * | 12/1991 | Vidusek | 239/290 |
| 5,235,969 | A * | 8/1993 | Bellm | 128/200.18 |
| 5,435,282 | A * | 7/1995 | Haber et al. | 128/200.16 |
| 5,579,757 | A * | 12/1996 | McMahon et al. | 128/200.21 |
| D395,494 | S | 6/1998 | Becker | |
| 5,797,389 | A * | 8/1998 | Ryder | 128/200.21 |
| D458,359 | S | 6/2002 | Blanchette | |
| 6,405,944 | B1 | 6/2002 | Benalikhoudja | |
| 6,796,513 | B2 * | 9/2004 | Fraccaroli | 239/338 |
| 7,143,763 | B2 * | 12/2006 | Abate | 128/200.14 |

* cited by examiner

*Primary Examiner*—Len Tran
*Assistant Examiner*—James S Hogan
(74) *Attorney, Agent, or Firm*—Bay Area Intellectual Property Group LLC.

(57) ABSTRACT

An improved atomization jet assembly for aromatherapy essential oil diffuser wells. It does not loose the cap during handling. It uses the capillary of liquids principal to draw essential oils between the exterior of the jet FIG. 12 and the inner cap profile FIG. 7. The flow of liquid is stopped by a capillary break 40. The Ventura principal is then used to create a low pressure area between the top of the jet ball 44 and the inside radius of the cap 65. An air/oil mixture blows out of the cap orifice 66 with the aid of an air pump. The net result is increased availability of air molecules attaching to oil molecules and making them airborne and breathable.

4 Claims, 12 Drawing Sheets

ATOMIZATION JET ASSEMBLY

CROSS-REFERENCE TO RELATED APPLICATIONS

Provisional Patent Application, Ser. No. 60/464,664 Filed Apr. 10, 2003

Design patent application, Ser. No. 29/179,375 Filed Apr. 10, 2003 (Now Issued) U.S. Pat. No. D491,258 S, Date of Patent: Jun. 8, 2004

Design patent application: Ser. No. 29/179,376 Filed Apr. 10, 2003 (Now pending)

Design patent application: Ser. No. 29/179,346 Filed Apr. 10, 2003 (Now Issued) U.S. Pat. No. D492,020 S, Date of Patent: Jun. 22, 2004

FEDERALLY SPONSORED RESEARCH

Not applicable

SEQUENCE LISTING OR PROGRAM

Not applicable

BACKGROUND OF THE INVENTION

1. Field of Invention

This invention relates to aromatherapy essential oil diffusers, specifically to an improved atomization jet assembly for essential oil diffuser wells.

BACKGROUND OF THE INVENTION

A rectangular essential oil diffuser well previously sold by Young Living Essential Oils Corporation, had some disadvantages and design problems. The jet cap would fall off during handling or cleaning. Customers would often loose the cap and have to order a replacement. The cap was a small object that became a great inconvenience to customers.

Two separate holes were drilled in the diffuser well body from opposite ends (94 and 98). The first hole 98 created an air passage through the center of a barb 99 and up through the center of the jet 95 (FIG. P7). A second hole 93 was drilled to connect oil well hole 91 to jet well hole 92 which allowed oil to pass from the oil well hole 91 to the jet well hole 92. An extra hole 93 required a second machining operation which increased manufacturing costs and had to be plugged and re-surfaced to hide plug 94 (FIG. 14). Plug 94 often showed up as "unattractive" after anodization due to color variation.

This design also spit and sputtered making undesirable noise. I found it was the distance between the air jet orifice 95 (FIG. P1) and the small hole in cap 97 (FIG. P1). This distance was created by a drill angle inside the cap 96 (FIG. P1) which often interrupted the venture action (Vacuum) because a portion of the air blew underneath the cap 96. This is largely what caused the sputtering and spiting of oils, operational inconsistencies and unpredictable output.

I found machining tolerances in manufacturing also effected performance of atomizing jet FIGS. P5 to P8. Too large of hole in the cap 97 affected the amount of low pressure created by venture action (Vacuum). Improper sizing of air jet orifice 95 would effect air flow and its ability to create venture action. Without proper air velocity delivered through air jet orifice 95 and incorrectly sized hole in cap 97 the assembly would spit and sputter large droplets of oil The gap, or distance between hole 95 and hole 97 becomes critical for breaking down (atomizing) oil particles efficiently, Management and employees of Young Living Essential oils corporation knew for years that the rectangular essential oil diffuser well (FIGS. P1 to P14) needed some improvement, but did not have acceptable options until now.

BACKGROUND OF INVENTION

2. Objects and Advantages

Having seen the manufacturing process of the prior art and evaluating the same consumer inconveniences for myself, I decided to design a new style of essential oil diffuser well, atomization jet, cap and glass diffuser with more attractive shapes and superior function. My system presents and overall feminine appeal which provides a better marketing edge over the prior art. The rectangular shaped prior art, diffuser well, atomization jet and glass diffuser are no longer manufactured. My jet and cap assembly was specifically designed to solve the disadvantages of the prior art in the following areas:

1. A Teflon rod was added which provides a dual function:
   - A- It creates tension between the jet and cap. The cap can be easily removed, but does not fall off, even if the diffuser well is turned upside down or shaken.
   - B- The lower end of the Teflon rod sticks down into the bottom of the jet slot and oil supply hole. This helps draw the oil from the lowest point of the diffuser jet well to the top of the capillary break.
2. A single hole drilled at 1 degree angle performs three functions.
   - A-It helps drain the oil from the oil well hole to the jet well hole.
   - B- It connects the oil well hole to the jet well hole. Drilling only one hole eliminated the unattractive plug and reduced extra machining operations.
   - C- It directs air to the jet. The jet acts as a plug that separates the air inlet from the oil reservoir. The jet seals the air cavity from the oil cavity.
3. Spitting, sputtering and noise were reduced by a consistent special relationship between the jet and cap. Machining tolerances held between the jet ball and the inside radius of the cap is critical. A maintained distance ensured consistent venture action (vacuum) created by the air velocity coming out of the jet orifice. A countersink angle on the cap hole aided the natural distribution of air/oil molecules in a fan shaped pattern. The net result of these design changes are improved performance and reliability of atomization.

Further objects and advantages of my invention will become apparent from a consideration of the drawings and ensuing description. Advantages covering the aesthetic appeal and better salability are covered in other design patents sited above.

SUMMARY

In accordance with the present invention, a Teflon rod, jet and cap comprises the entire 3 component assembly. The jet acts as a plug to divide the air supply from the oil supply. A carefully engineered gap tolerance between the jet and cap create dependable atomization. This assembly must then be pressed into a diffuser well to complete a functional system that supplies air and oil to the jet for atomization.

DRAWING

FIGURES

FIG. 1 illustrates an assembly view of my 3 component atomization jet. A Teflon rod 70 must be inserted into slot 36 before a cap 60 is placed over jet 30. The assembly does not become a functioning system until it has been pressed into some type of diffuser well designed for it. The shape of the diffuser well does not matter, only that it meets functional design criteria for the atomization jet assembly.

FIG. 2 Front elevation view where the Teflon rod is shown underneath the cap.

FIG. 3 Bottom plan view showing only a portion of the rod, hidden lines indicate the rest is hidden from view.

FIG. 4 Right elevation view showing the rod protrudes out slightly. This protrusion will later be pinched inside a diffuser well to hold it in place.

FIG. 5 Top plan view

FIG. 6 Front elevation view

FIG. 7 Section view to show inside and outside diameter relationships.

FIG. 8 Bottom plan view showing sectional cut line.

FIG. 9 Rear elevation view showing the optional horizontal air inlet hole.

FIG. 10 Bottom plan view

FIG. 11 Top plan view

FIG. 12 Front elevation view showing the slot.

FIG. 13 Left side elevation view showing inner hole relationship to the outside diameter.

FIG. 14 Right elevation view shows slot and taper relationship to the outside diameter.

FIG. 15 Section view showing inner structure of jet

FIG. 16 Front elevation view of Teflon rod.

FIG. 16B Top plan view of Teflon rod

FIG. 17 Bottom plan view of jet showing section line reference.

FIG. 18 Sectioned assembly view showing air and oil flow paths

FIG. 19 Top plan view of jet receptacle in well

FIG. 20 Section view of jet receptacle

FIG. 21 Section view of jet pressed into jet receptacle

FIG. 22 Top plan view of jet pressed into an oval shaped diffuser well

FIG. 23 Front elevation view of jet pressed into an oval shaped diffuser well FIG. 24 Top plan view of jet pressed into an round shaped diffuser well FIG. 25 Front elevation view of jet pressed into an round shaped diffuser well FIG. 27 Section view of oval or FIG. 8 shaped diffuser well showing jet location FIG. 28 Top plan view of FIG. 8 shaped diffuser well

DETAILED DESCRIPTION

FIGS. AND PREFERRED EMBODIMENT

FIG. 15 shows an atomization jet assembly for an aromatherapy device, which comprises of a jet and a jet cap, in which: A jet comprises of:

- a top end;
- a bottom end;
- a capillary break near the top end; and
- a cavity extending from the bottom end to said top end wherein the top end has an orifice leading to said cavity. The bottom end has an opening therein which leads from an outer surface of the jet to the cavity.

Figure 1:
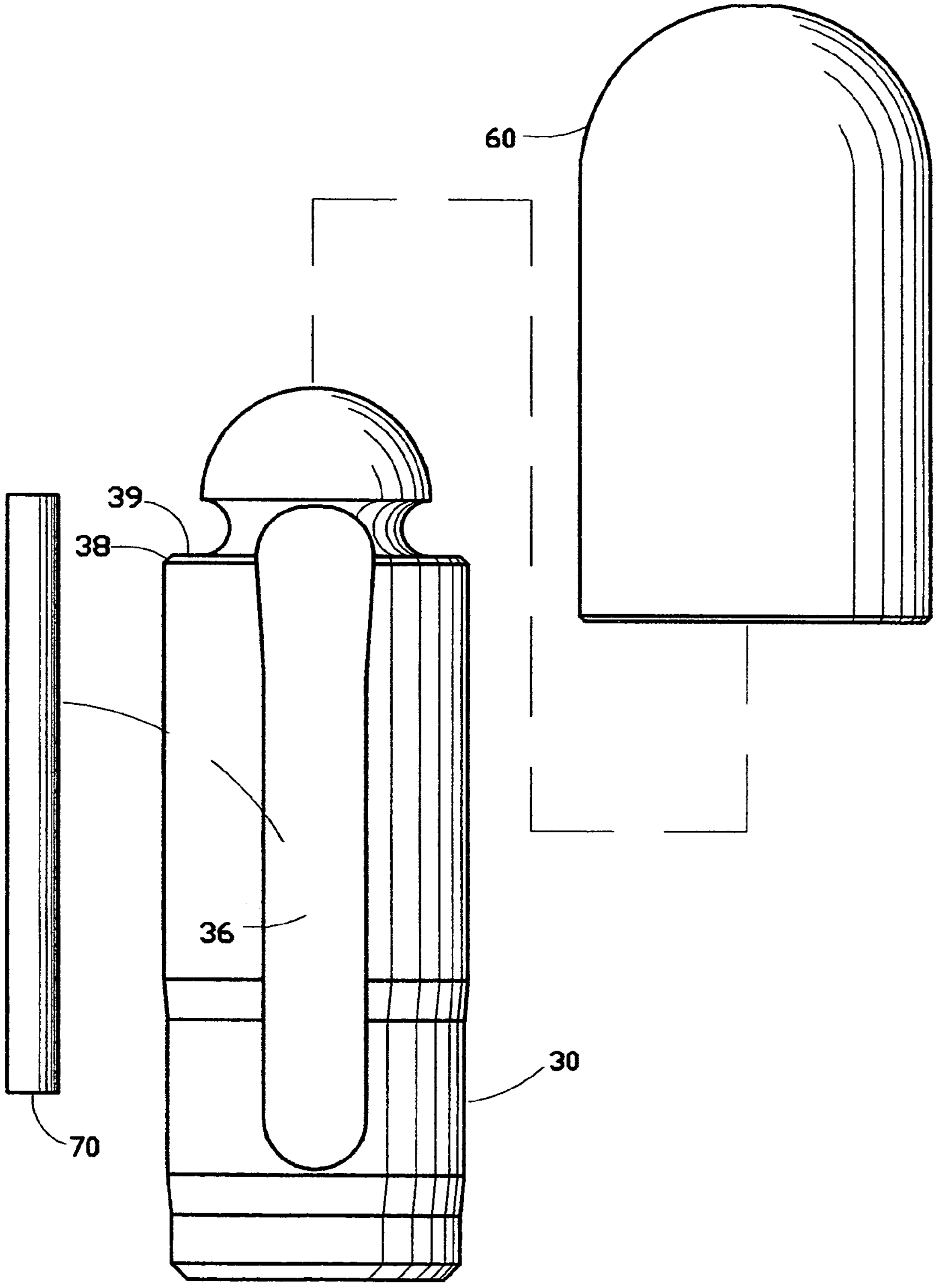
FIG. 1 shows the atomization jet assembly of both said jet and said cap have a cylindrical profile. Although a round shape is not necessary, it is a preferred method of manufacturing for ease of machining.
Figure 2:
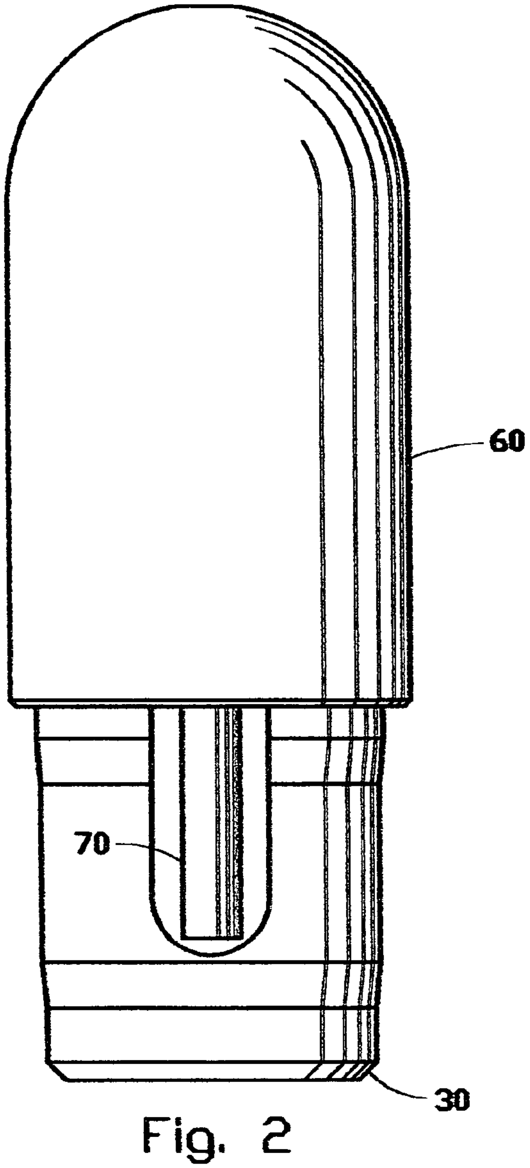
Figure 4:
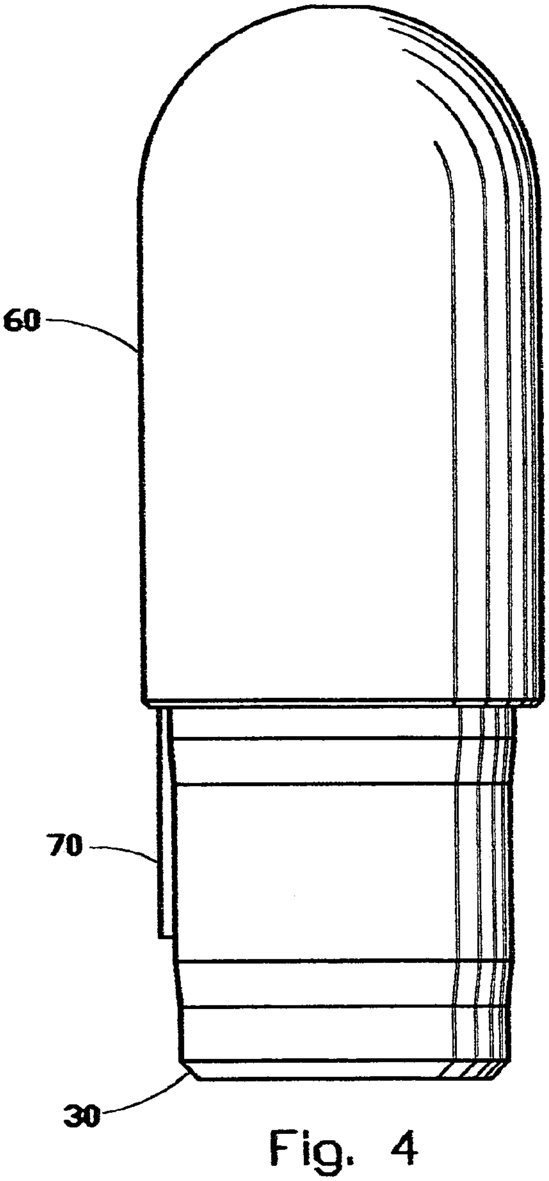
Figure 3:
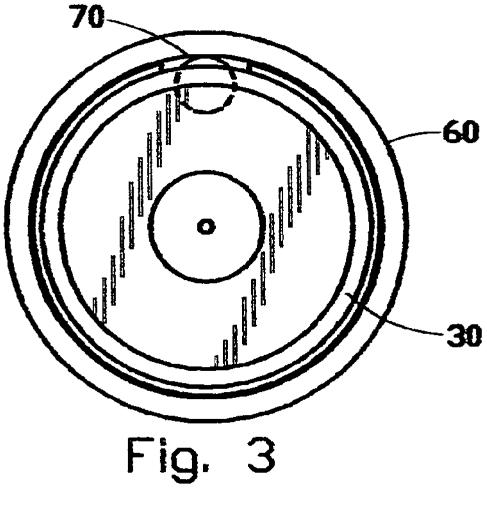
Figure 5:
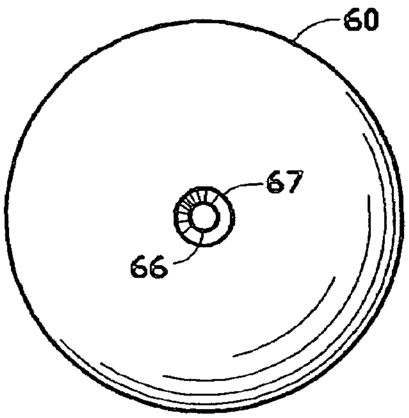

Any shape could be used to create capillary action. Such as Triangular, square, oval, rectangle, trapezoid, pyramid, octagon, hex or any other form or combination of forms could be used. The shape of a cap being adapted to fit over a jet from the top end of said jet toward the bottom of the jet wherein the shapes of the jet and cap are similar in profile, such that a capillary space exists between said jet and said cap.

FIGS. 22 through 28 show that any shape of base structure that has a top surface, a bottom surface, and an outer surface connecting said top surface and said bottom surface, and that comprises a cavity therein, can be adapted to receive the bottom end of said jet.

A particulate separator can be adapted to fit over, around or in close proximity to the atomization jet assembly with the bottom surface of said particulate separator and may rest in any cavity or receptacle in the base.

DETAILED DESCRIPTION

FIGS. AND PREFERRED EMBODIMENT (continued)

The jet and cap are typically manufactured on standard screw machines with specialized tooling or CNC lathes with standard tooling and specialized programming. Any conventional or modernized machine shop with the proper equipment can make these parts. There is really nothing special about the manufacturing process other than maintaining the tolerances listed on the prints. The jet and cap can be made of any machineable or injection moldable material that maintains structural integrity after manufacture. Some materials are preferred because of their chemical resistance or aesthetic properties. Materials typically used are anodized aluminum, stainless steel or oil resistant polymers.

A cap FIGS. 5-8 is a cylindrical object with a dome shape on one end and flat on the other. A countersink 67 and through hole 66 are drilled in the center of a dome 61. Bottom edges are chamfered 62 which make a transition to an inside diameter 63 and outside diameter 60. A diameter change 64 inside the cap leads to an inside radius 65 and to a through hole 66. Surface finish on the cap is typically very smooth. The cap fits symmetrically about the axis of a jet.

Figure 12:
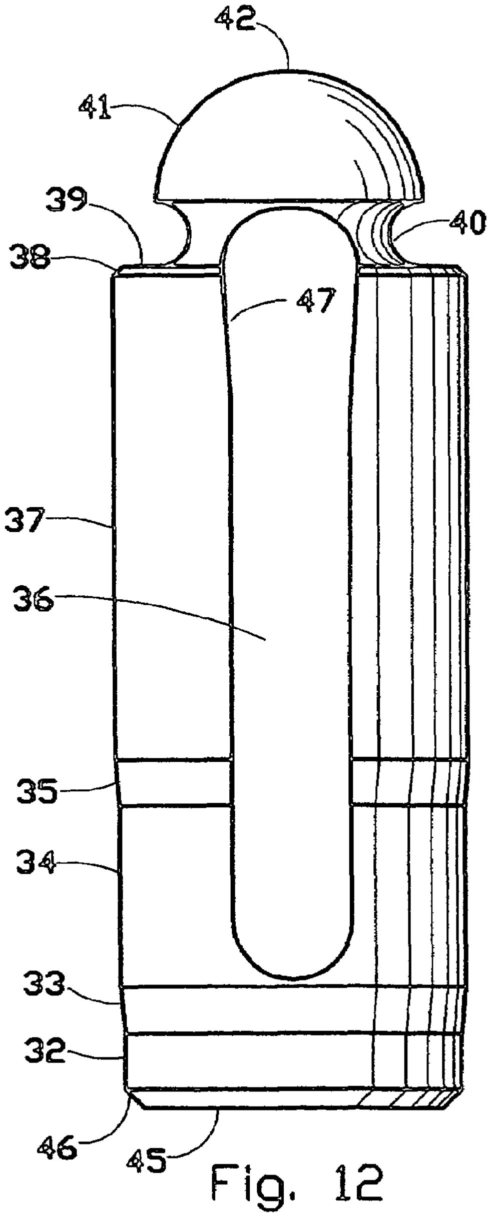
Figure 13:
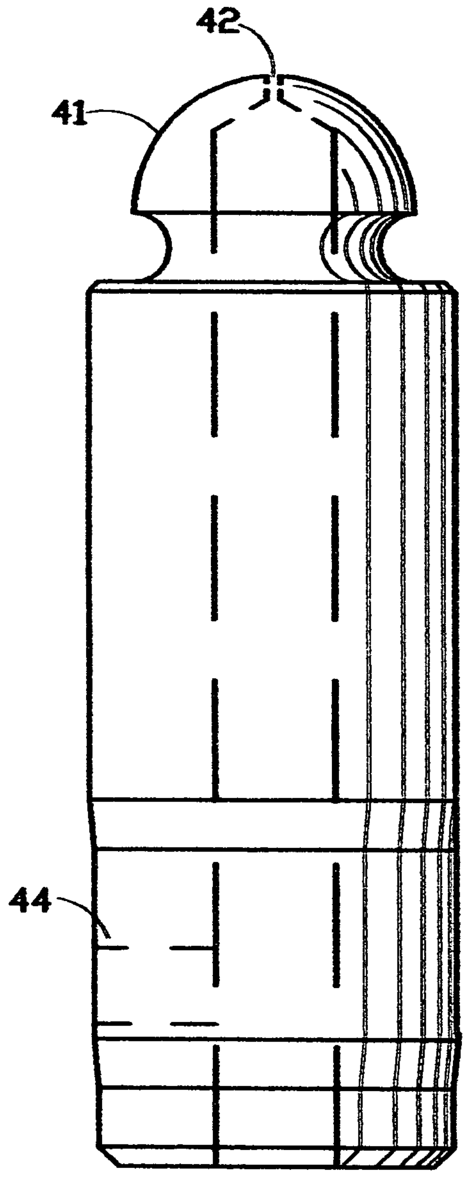
Figure 14:
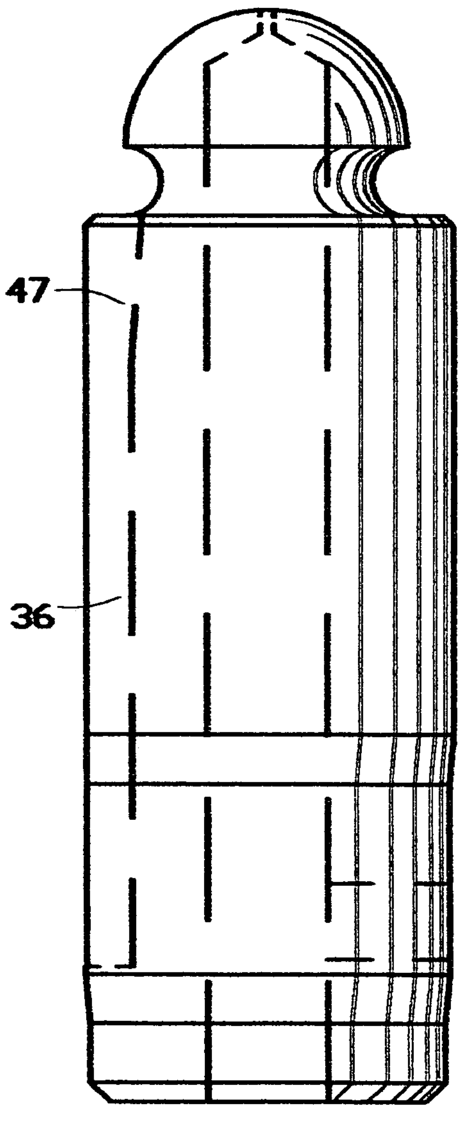

A jet is a cylindrical shaped object with three diameter changes on the body and two tapered transitions. (Ramification: Angular and diameter transitions are not necessary to the function of the system, but they are helpful in forming a positive seal during assembly) FIG. 12 shows a flat surface 45 on the bottom of the jet is chamfered 46 to create a lead in angle during assembly. A small diameter 32 is connected to a transition angle 33 that is approximately 0.050" long. Intermediate diameter 34 is in between transition angles 33 and 35. Transition angle 35 is typically the same length as 33 and connects to the large diameter 37. Chamfer 38 must maintain a fairly tight machining tolerance +/−0.002" with respect to surface 39 and large diameter 37. A capillary break 40 is formed near the top of the jet and underneath a ball radius 41.

Figure 9:
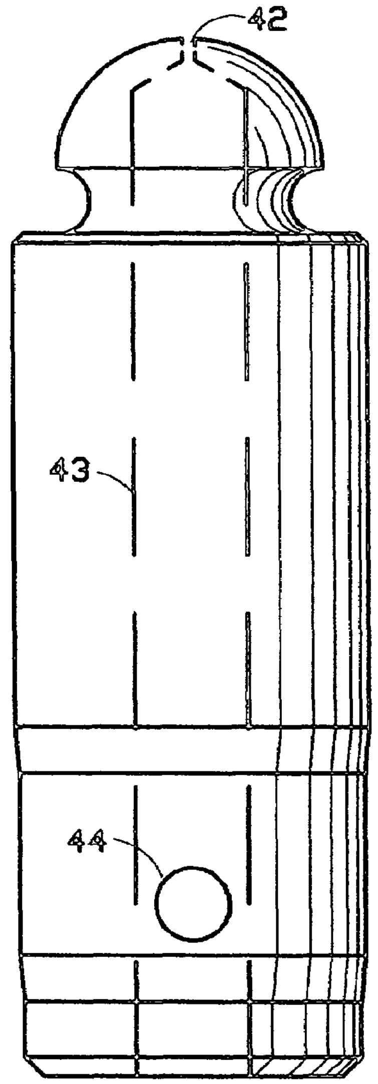
Figure 10:
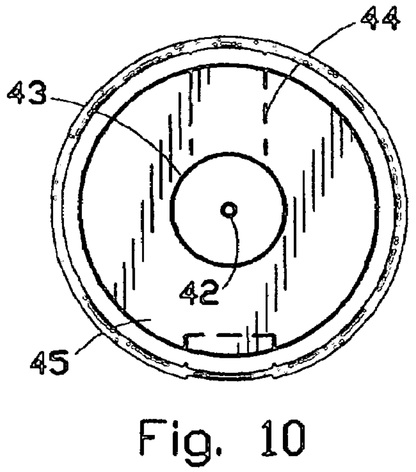
Figure 11:
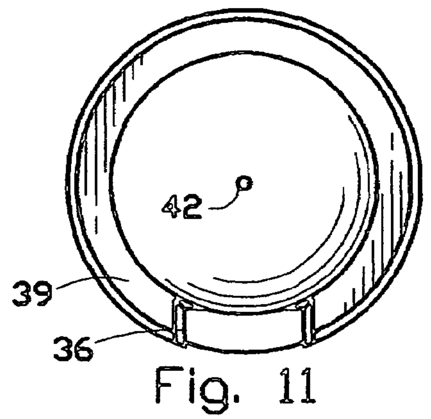
Figure 15:
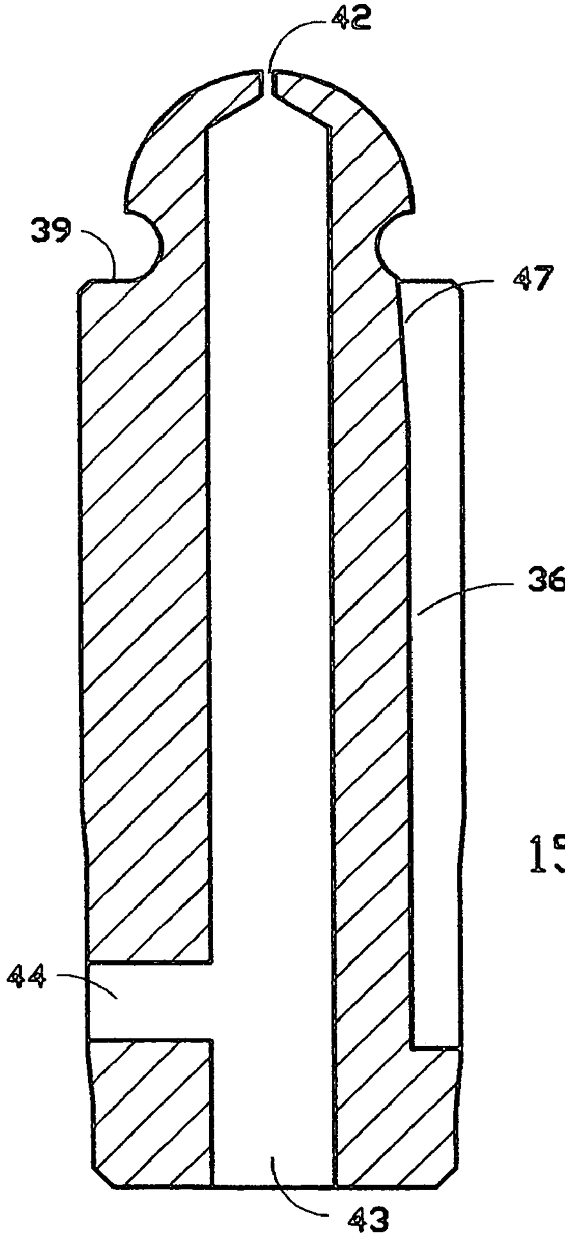
Figure 17:
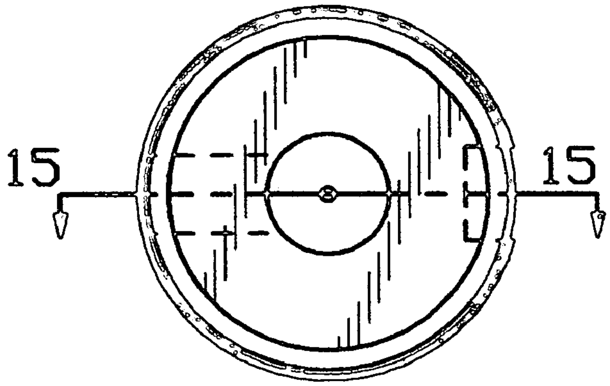

A small hole 42 is drilled in the center of ball radius 41 and concentric to large diameter 37. The depth of hole 42 should be a minimum of 1.5 times the diameter of hole 42. A slot 36 is machined into the jet and ranges in width from 0.075" to 0.125" in typical applications. A bi-directional taper 47 is added to facilitate cap insertion over the jet and angles outward and downward towards the center of ball radius 41. A hole 43 is drilled through the center axis of the jet FIG. 15 and stops approximately 0.020" from exiting ball radius 41. In some applications a hole 44 FIG. 9 and FIG. 15 is drilled parallel to flat surface 45 and 180 degrees from slot 36. This hole is located near transition angle 33, Hole 44 is not used where the diffuser well design supplies air from the bottom FIG. 25. All surface finishes should be smooth to reduce contamination collection.

Figure 16:
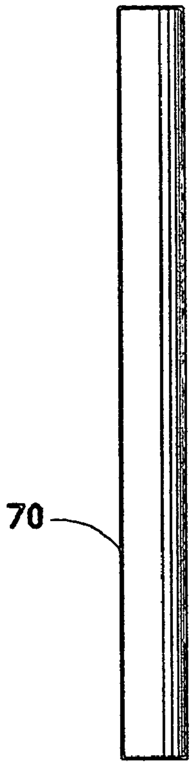
Figure 16B:

A 1/16" diameter Teflon rod FIGS. 16 and 16B is cut to length depending on the jet height. The ends can be cut square or tapered and usually requires some type of crimp on one end before inserting it into the jet and diffuser well assembly.

Figure 20:
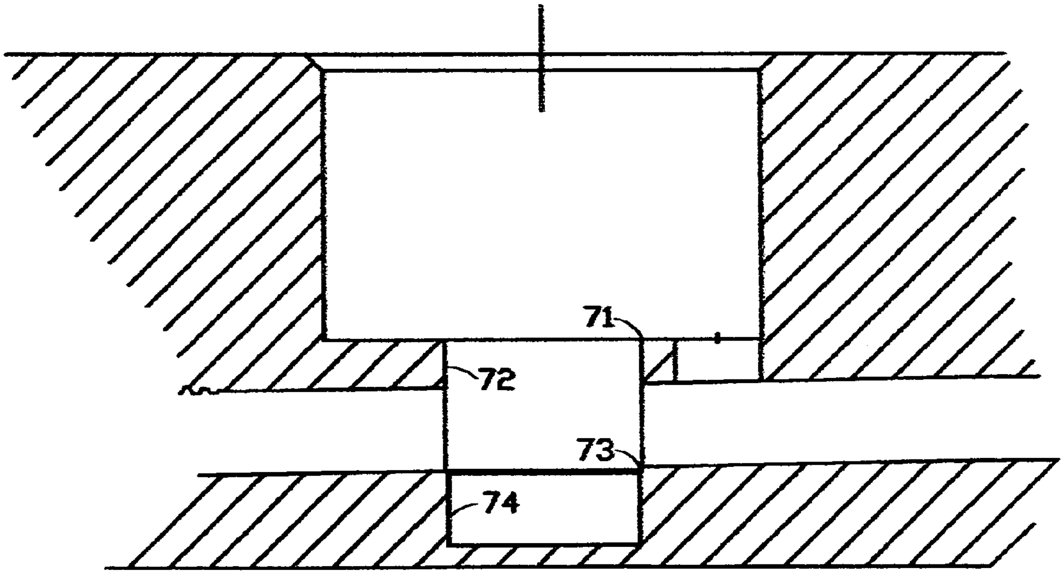

A jet hole inside a jet well FIG. 20 is required to complete the atomizing jet system. Diameter interference tolerances of 72 and 74 are critical for proper seal between air supply 86 and oil supply 80, FIG. 8. Diameter transitions 71 and 72 are critical with reference to angular transitions 33 and 35. Although diffuser well patents are not covered by this application, I have included FIGS. 22 to 25 to show a few alternatives in diffuser well designs and how the jet assembly is used. (Ramification: There is really no limit to the diffuser well designs that can use the same jet assembly).

The process of inserting the jet requires a diffuser well of any shape or size. A special insertion tool (not shown) must be designed to fit over the jet ball radius 41 and seat on shoulder 39. The tool must be designed so the pressure required to insert the jet does not distort jet diameter 37, chamfer 38 or shoulder 39. Chamfer angle 46 helps guide the jet into the jet well hole FIG. 20. Approximately 0.002" interference should exist between diameters 32, 34 and 72, 74 after anodization. (For raw aluminum jets and diffuser wells this interference should be about 0.0035" ). Angular transition areas 33 and 35 will distort and crush onto diameter transitions 71 and 73. This crushing action and diameter interference will form a positive seal between the air supply 86, oil supply 80 and diffuser well hole 84. If all these surfaces do not seal properly, air bubbles will exit through the oil supply side 80 or through the jet well 84.

After the jet has been installed, a special tool (not shown) is required to insert the Teflon rod between slot 36 and diameter 72. Crimping the end of the Teflon rod makes it easier to insert into the opening. As the Teflon rod is pushed to the bottom of the opening it becomes distorted and maintains its position by the tension created by distortion.

Figure 7:
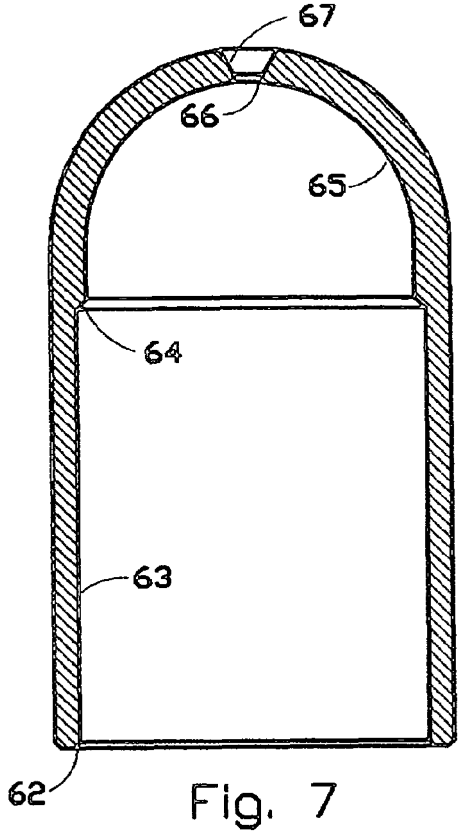
FIG. 7 shows a section view of a cap which comprises of a hollow shaped structure having a top end and a bottom end where the top end has a orifice which is in alignment with the orifice of said jet. The shape of the cap is adapted to fit over the jet from the top end of said jet toward the bottom end of said jet.
Figure 6:
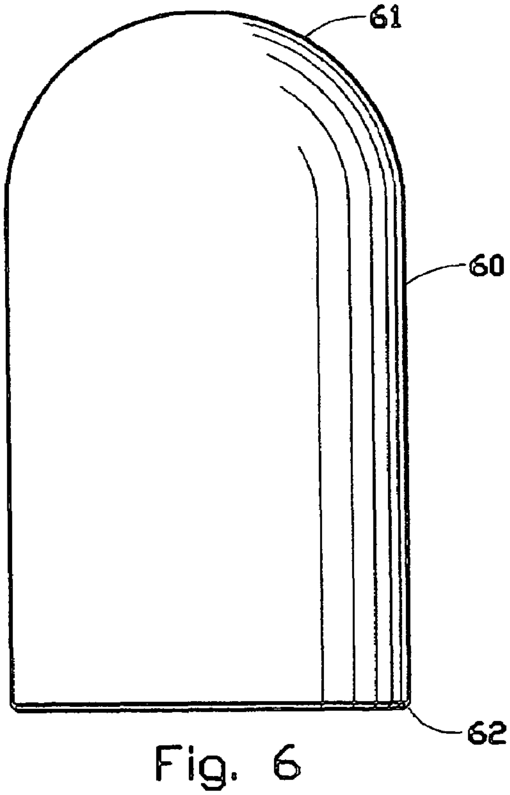
Figure 8:
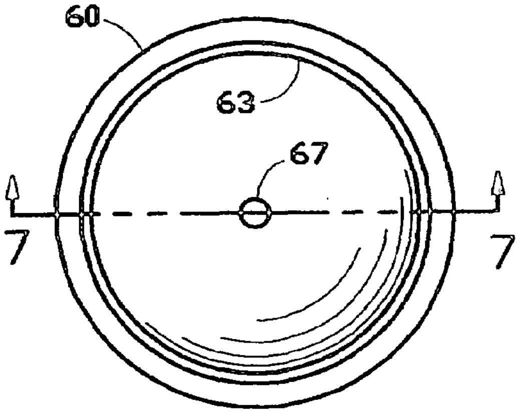

A cap FIG. 1, is slipped over the jet and pushed down until diameter change 64 FIG. 7 rests on chamfer 38. At this point the atomization jet assembly is complete and ready for use. (Do I need to provide a description for FIGS. 22 to 25 and the prior art drawings?)

OPERATION OF THE INVENTION

Figure 18:
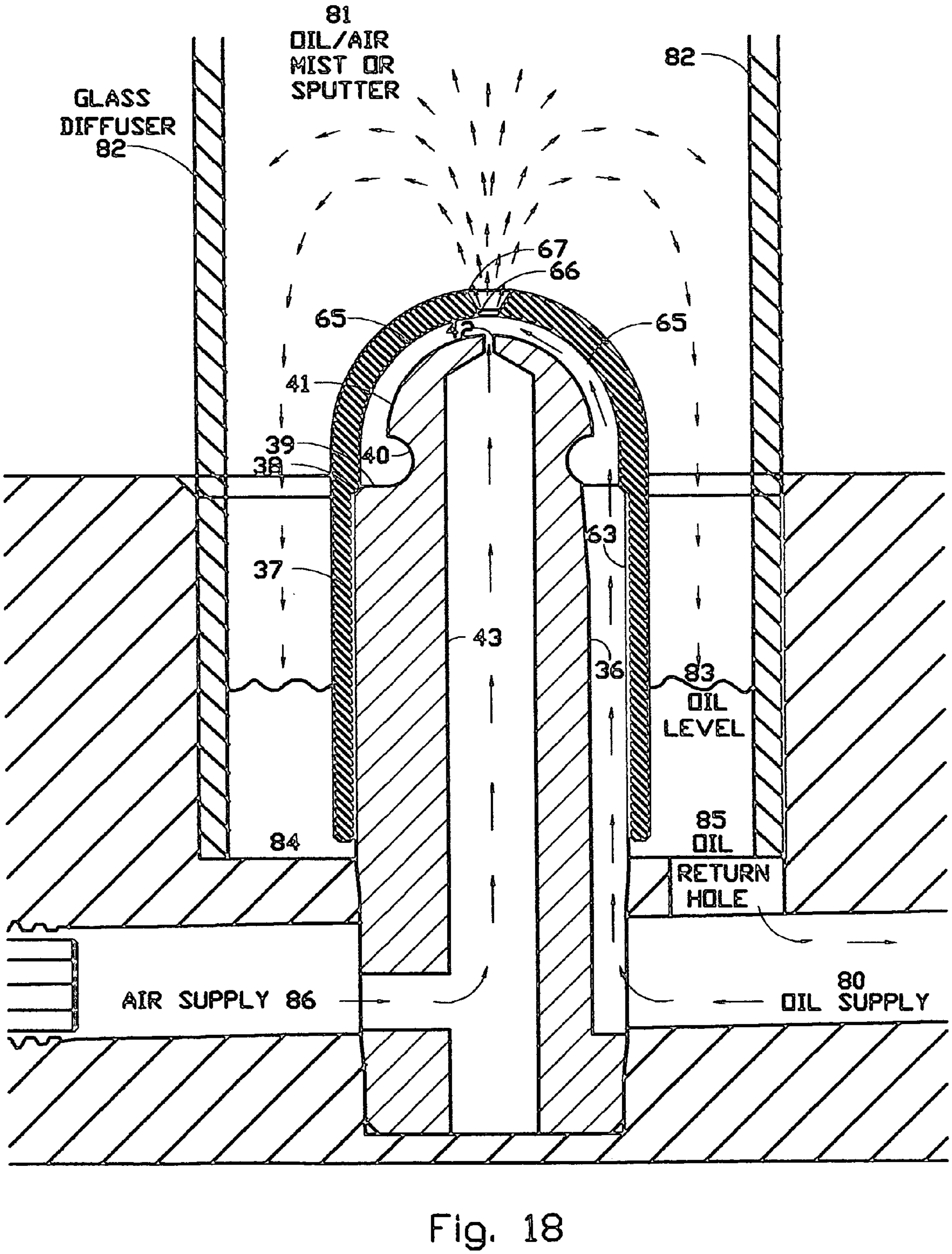
Figure 19:
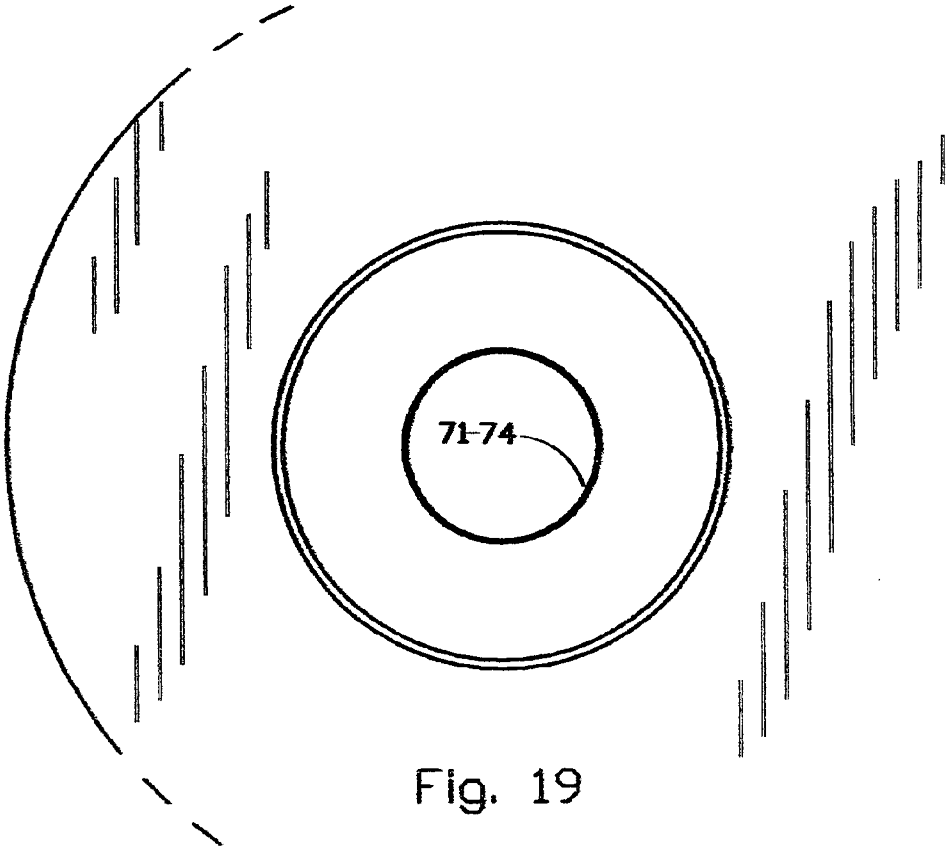

As illustrated in FIG. 18 an air supply 86, requires aproximatly 1 psi and 400 cubic centimeters per minute air flow to begin atomization. As the air travels through hole 43 and out small hole 42 it creates a low pressure area (better known as the Ventura principal) at the top of ball radius 41. The gap between ball radius 41 and inside cap radius 65 acts as an enclosure around the low pressure area. An oil (or liquid) present in oil supply hole 80 is drawn up slot 36. Slot 36 provides an easy flow path for the oil or liquid. As the oil reaches the top of ball radius 41 it mixes with air exiting small hole 42. An air/oil mixture now sprays out through hole 66 in an upward direction. The oil/air mixture may create a spray pattern ranging from a fine mist to a sputtering of large droplets depending on the viscosity of the oil. A glass diffuser 82 is inserted into jet well hole 84 to separate large oil particles from airborne particles. (Please see design patent for Glass diffuser) The large particles are returned to jet well 84 and airborne particles are carried out the top of glass diffuser 82 with the escaping air flow. When air supply 86 is turned off, back siphoning of oil into small hole 42 is prevented by capillary break 40. Gravity pulls oil down to the open area created by radius 40. Without capillary break 40, oil could enter small hole 42 and begin filling air supply chamber 86 by way of capillary. If oil were to fall down hole 43 it would create a suction and keep pulling more oil through hole 42. This process would keep going until jet well 84 is empty. Oil is suspended around surface 39 and chamfer 38 due to capillary tension between large Jet diameter 37 and inside diameter 63 of the cap. Capillary tension is also created by jet slot 36, Teflon rod 70 (not shown in FIG. 18) and inside cap diameter 63. Capillary break 40 is very important because it stops back siphoning.

A slot 36 is machined into the side of the jet FIG. 15 to provide a place for a 1/16" diameter Teflon rod FIG. 16 to rest. FIG. 1 shows the Teflon rod as the locking component that holds the cap onto the jet. Tension between the cap and jet is accomplished by compressing or deforming the Teflon rod 0.003 to 0.007 inches. It is important to maintain resiliency of the Teflon rod by not compressing it too much.

If the jet is stainless steel, both diameters 32 and 34 should have about a 0.002" interference fit after anodization with reference to the diffuser well jet hole 72 and 74 (See FIG. 12). If a raw aluminum jet is pressed into a raw aluminum well, the interference tolerance should be about 0.0035 inches. Once the jet is pressed into place, the interface fit creates a seal between the air inlet cavity 86 and the oil supply hole 80 (FIG. 18). The tapered sections on jet 33 and 35 crush against the lip 71 and 73 inside the jet well hole FIG. 20. This crushing action of material creates a positive sealing ring between the air inlet cavity 86 and all oil containment areas. The entire system relies upon these interface fits and crushing rings to separate the oil cavities from pressurized air. If these seals fail, the diffuser will blow bubbles into the oil or leak oil into the air supply line. Any seal failure is undesirable and renders the assembly useless.

Operation of Invention

Air supply 86 can be turned on before or after oil is added to the diffuser well. The glass diffuser 82 (F*ig*. 18) should be in place prior to starting air flow. This will prevent liquid or oil from blasting out onto the table or other areas.

Once oil contacts the bottom parameter of cap 62 (FIG. 6) it will begin pulling oil vertically by way of capillary through jet slot 36 and between the Teflon rod (FIG. 16) and inner cap diameter 63 (FIG. 7). Capillary action will move the oil with or without air flowing through the jet. Oil or liquid may be pulled as high as capillary break 40 (FIG. 12). If oil does pass between ball radius 41 and inside radius 65 without air flowing through the jet orifice 42, then the jet well 84 (FIG. 18) is too deep and/or the oil level 83 is too high. With a properly designed jet well this should never happen. The capillary break 40 is designed to stop the flow of liquid from getting into the air supply line. The only exception to this rule would be the un-intended use of a vacuum pulling or air flowing in the reverse direction of the air supply channel 86 (FIG. 18).

Under normal and intended use, this has never been a problem. Even with the jet well full of oil and the air supply turned off during operation, the oil will pull away from jet orifice 42 and move down the jet ball radius 41 towards the capillary break 40.

Oil cannot, under normal circumstances, be pulled up around jet ball 41 and exit the cap hole 66 without assistance of the Ventura action (vacuum) created by the air velocity 86 flowing through the jet orifice 42. A low pressure area is created between the top of the jet ball 44 and the inner cap radius 65 as air exits the hole in the top of the cap 66 & 67. Oil is also drawn out with the air and the net result is an increased availability of air molecules mixing with oil molecules. These molecules or particles are carried into the glass diffuser tube 82. The larger particles fall back into the jet well. The majority of oil particles are collected onto the inner surfaces of the glass diffuser and returned back to the jet well 84. (see design patent application for glass diffusers). Typically the smaller, airborne molecules are carried out of the top of the glass diffuser 82. A visibly detectable mist or fume usually comes out the top of the glass diffuser. Sometimes it has the appearance of a smoke stream, some times it is not visible. The rate of atomization depends on the viscosity and properties of the liquid. Sometimes it is easier to tell if the diffuser is atomizing by smelling the top of the glass diffuser or watching the oil come out of the cap hole 66 & 67.

CONCLUSION, RAMIFICATIONS, AND SCOPE OF INVENTION

Thus we see that customers are happier about the cap maintaining its position on the jet, so it does not get lost. Out of 18,000 sold since the provisional patent application was filed, no one has requested a replacement for the cap. We also see that the system works more reliably and consistently with a more shapely and attractive form.

The above descriptions and specifications should not be construed as limitations on the scope of the invention, but as exemplification's of one preferred embodiment. Many other variations are possible. For example: The jet and cap can be made of numerous materials. In fact, the jet could be molded as part of the diffuser well. Clear plastic caps could be used to monitor the movement of the liquid.

The assembly will work just fine without the Teflon rod. Holding the cap in place is not required. The size, shape tolerances, colors and length of the cap and jet could all be changed and still meet functional criteria.

Figure 21:
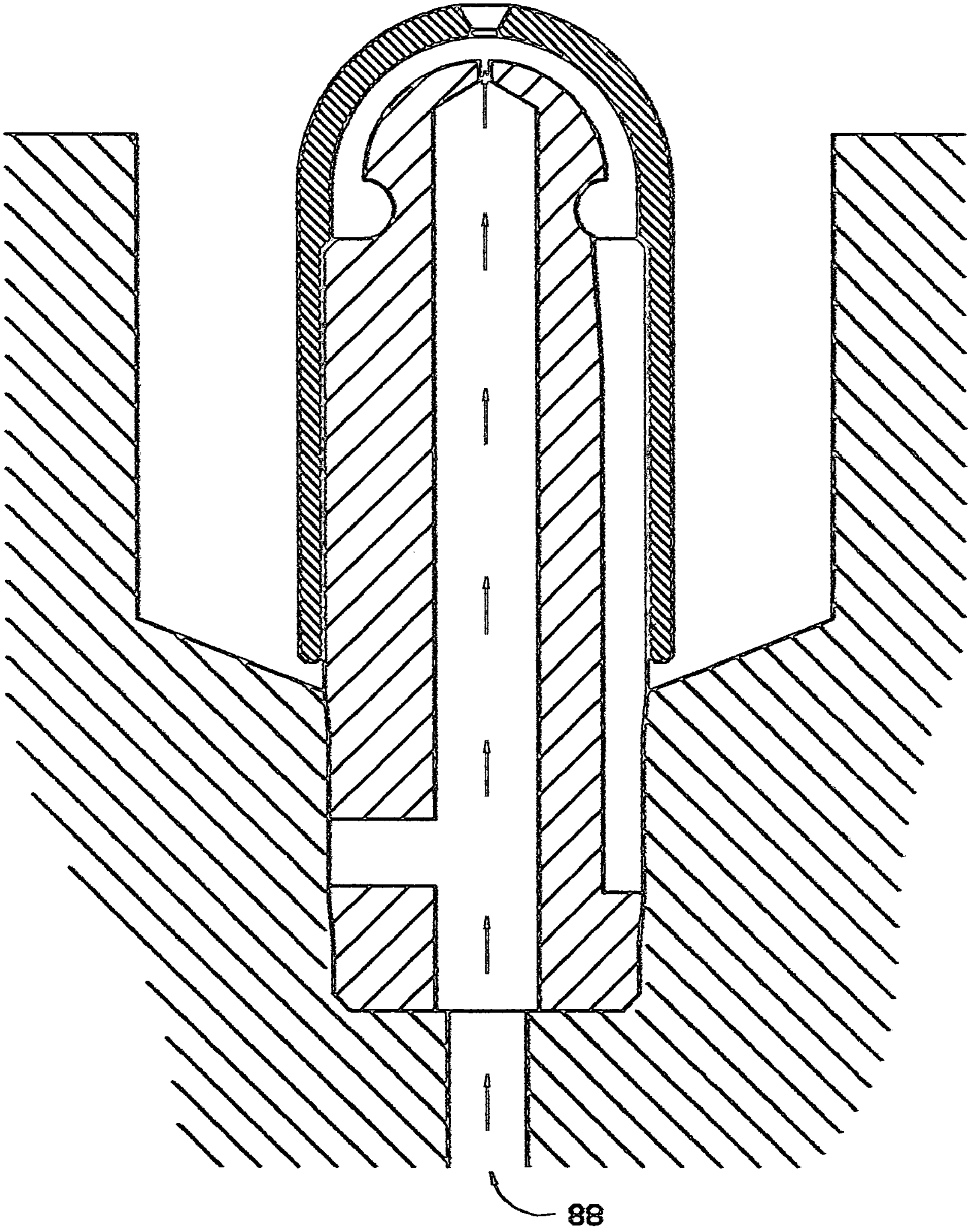
FIG. 21 shows the shapes of said jet and said cap are similar in profile, such that a capillary space exists between the jet and cap. Capillary; is defined as the action of drawing a liquid between two surfaces in close proximity to each other.
Figure 22:
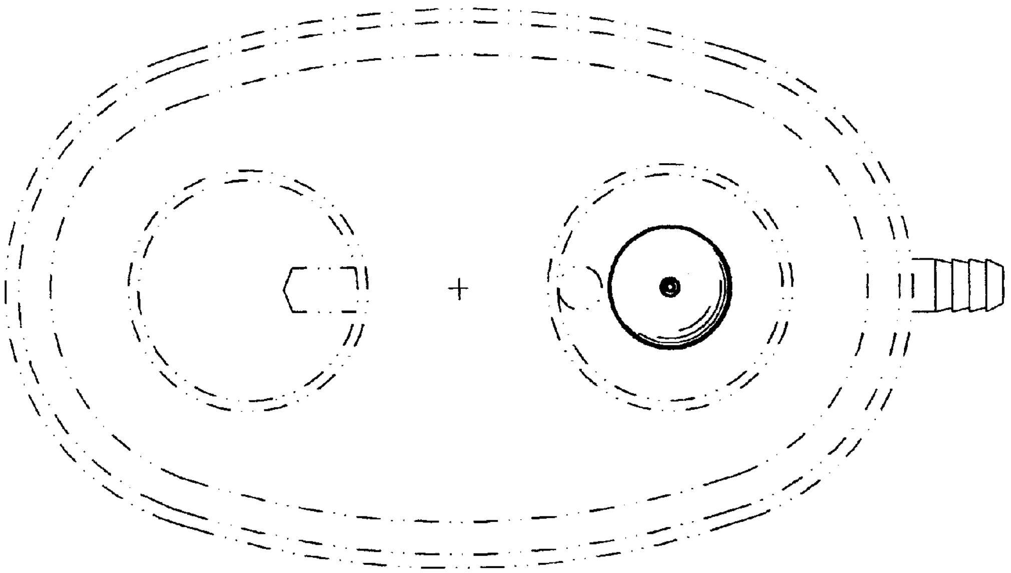
Figure 23:
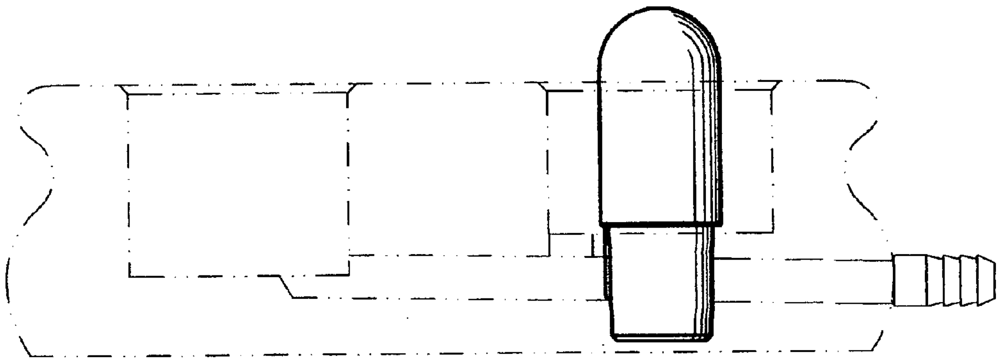
Figure 24:
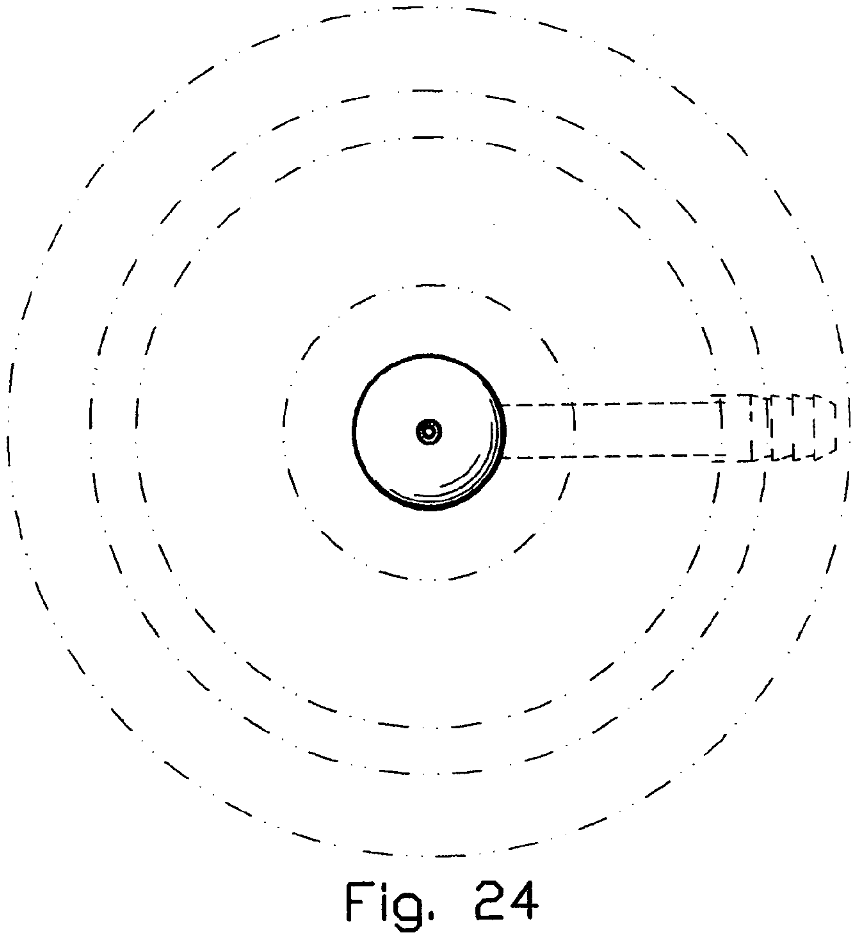
Figure 25:
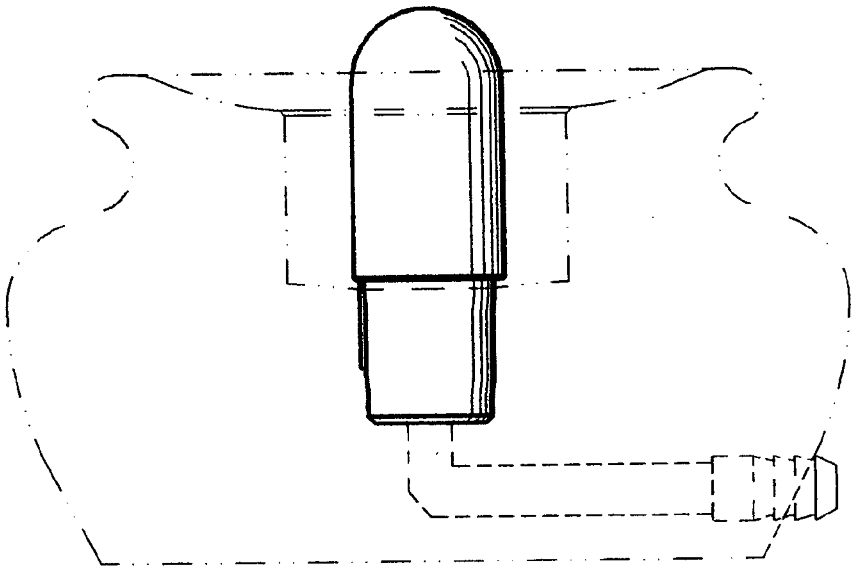
Figure 27:
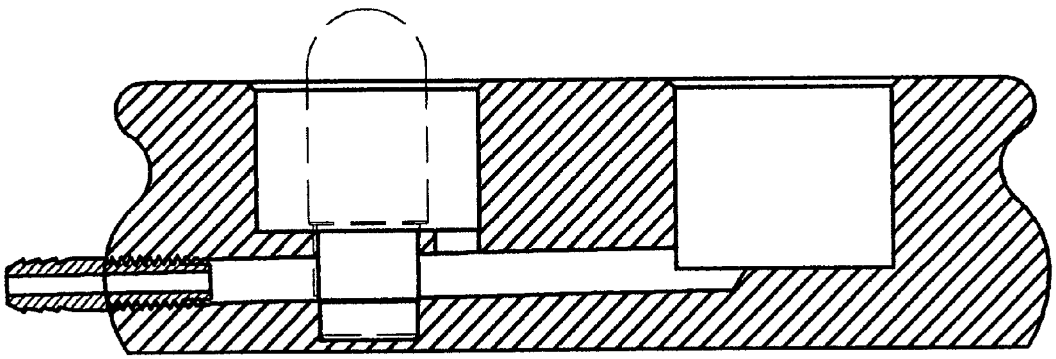
Figure 28:
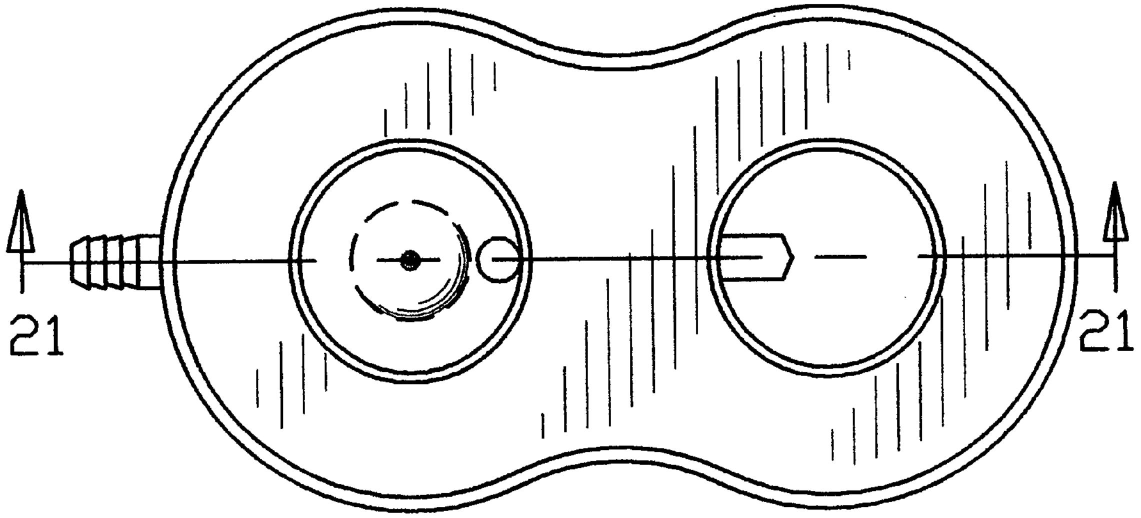

The jet does not require an oil supply hole coming from a secondary oil well hole as illustrated FIG. 18. FIGS. 22 through 28 show other shapes of diffuser wells. FIG. 21 shows air access from below the jet instead of from the side of the jet.

Accordingly, the scope of the invention should be determined by the claims and their legal equivalents, not by the illustrated embodiments.

What is claimed is:

1. An atomization jet assembly for an aromatherapy device using a fluid the assembly comprising:

a jet comprising:

a top end;

a bottom end;

a capillary break positioned circumferentially on an exterior surface of said jet approximate said top end and shaped to provide a break in capillary action;

a slot positioned vertically on said exterior surface, said slot extending from said capillary break to a point approximate said bottom end;

a rod dimensioned for insertion in said slot where, when said rod is inserted in said slot, said slot and rod provide a capillary action; and a cavity extending from said bottom end to said top end; in which:

said top end comprising an orifice leading to said cavity; and said bottom end comprising an opening leading from said exterior surface of said jet to said cavity to supply pressurized air to said cavity; and a jet cap comprising:

a hollow shaped structure comprising a top end and a bottom end; in which:

said top end comprising an orifice which is in alignment with said orifice of said jet; and the shape of said jet cap being adapted to fit over said jet from the top end of said jet toward the bottom of said jet;

wherein the shapes of said jet and said jet cap are similar in profile, such that capillary action exists between said jet, said jet cap, said slot and said rod and said jet cap is retained in place over said jet by tension between said jet cap and jet by compression of said rod by said jet cap.

2. The atomization jet assembly of claim 1, in which both said jet and said jet cap have a cylindrical profile.

3. An aromatherapy device which comprises using a fluid, the device comprising:

an atomization jet assembly, a base structure, and a particulate separator having a top end and a bottom end; in which: comprising:

said atomization jet assembly comprises;

a jet and a jet cap, in which:

said jet comprises:

a jet comprising:

a top end;

a bottom end;

a capillary break positioned circumferentially on an exterior surface of said jet approximate near said top end and shaped to provide a break in capillary action;

a slot positioned vertically on said exterior surface, said slot extending from said capillary break to a point approximate said bottom end;

a rod dimensioned for insertion in said slot where, when said rod is inserted in said slot, said slot and rod provide a capillary action; and a cavity extending from said bottom end to said top end;

in which:

said top end comprising an orifice therein leading to said cavity; and said bottom end comprising an opening therein which leads leading from an outer said exterior surface of said jet to said cavity; and said a jet cap comprises comprising:

a hollow shaped structure having comprising a top end and a bottom end; in which:

said top end has a comprising an orifice there through which is in alignment with said orifice of said jet; and the shape of said jet cap being adapted to fit over said jet from the top end of said jet toward the bottom of said jet; wherein where the shapes of said jet and said jet cap are similar in profile, such that capillary space action exists between said jet, said jet cap, said slot and said rod and said jet cap is retained in place over said jet by tension between said jet cap and jet by compression of said rod by said let cap; and said a base structure comprising a top surface, a bottom surface, and an outer surface connecting said top surface and said bottom surface, wherein:

said top surface comprising a cavity therein adapted to receive said bottom end of said jet and said bottom end of said jet cap where a level of fluid in said cavity is above said bottom end of said jet cap. particulate separator; and said outer surface comprising an opening therein which leads to said cavity in said top surface of said base structure to supply pressurized air to said opening in said bottom end of said cavity of said jet said particulate separator is adapted to fit over said atomization jet assembly with the bottom surface of said particulate separator resting in said cavity of the top surface of said base.

4. The aromatherapy device of claim 3, in which both said jet and said jet cap of said atomization jet assembly have a cylindrical profile.

* * * * *